United States Patent [19]
Nunokawa

[11] Patent Number: 4,834,526
[45] Date of Patent: May 30, 1989

[54] EYE FUNDUS CAMERA HAVING AUTOMATIC EXPOSURE CONTROL MEANS

[75] Inventor: Kazuo Nunokawa, Tokyo, Japan

[73] Assignee: Tokyo Kagaku Kikai Kabushiki Kaisha, Tokyo, Japan

[21] Appl. No.: 122,551

[22] Filed: Nov. 13, 1987

Related U.S. Application Data

[63] Continuation of Ser. No. 15,556, Feb. 12, 1987, abandoned, which is a continuation of Ser. No. 598,842, Apr. 10, 1984, abandoned.

[30] Foreign Application Priority Data

Apr. 13, 1983 [JP] Japan .................................. 58-65022

[51] Int. Cl.⁴ .......................... A61B 3/14; G03B 29/00
[52] U.S. Cl. ....................................... 351/206; 354/62
[58] Field of Search .................. 351/206, 210; 354/62, 354/423

[56] References Cited

U.S. PATENT DOCUMENTS 4,429,970 2/1984 Fujiwara .............................. 351/206
4,563,070 1/1986 Saito et al. ........................... 354/423

Primary Examiner—Rodney B. Bovernick
Assistant Examiner—P. M. Dzierzynski
Attorney, Agent, or Firm—Brumbaugh, Graves, Donohue & Raymond

[57] ABSTRACT

An eye fundus camera including an illuminating optical system having a photographing light source such as a xenon lamp, and a photographing optical system having an image forming lens and a photographing film plane. A light measuring system is provided and includes a half mirror disposed in the photographing optical system to reflect a part of light passing through the photographing system, the reflected light being received by a photodetector. The signal from the light measuring system is used to control the operation of the xenon lamp to thereby control the exposure. The light measuring system includes a variable aperture device conjugate with the film plane, the aperture device having a plurality of apertures of different diameters so that the field of measurement of light can be changed in accordance with the photographing field.

5 Claims, 4 Drawing Sheets

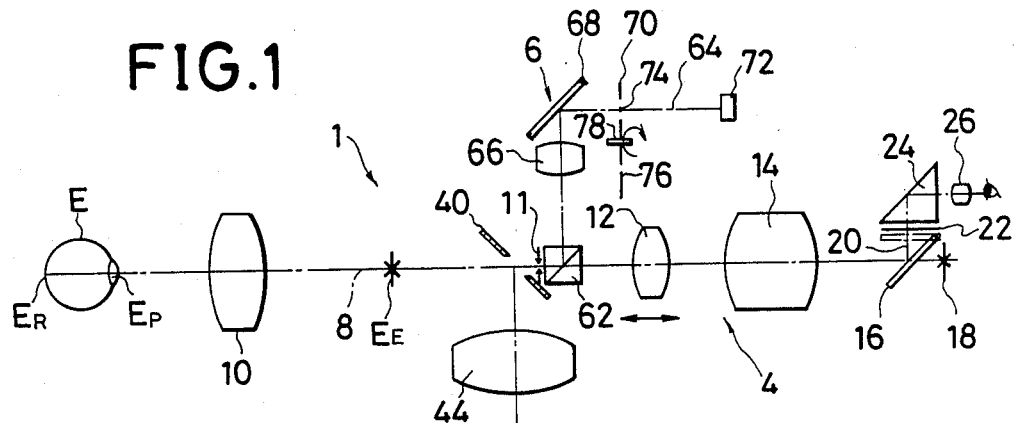
FIG.1
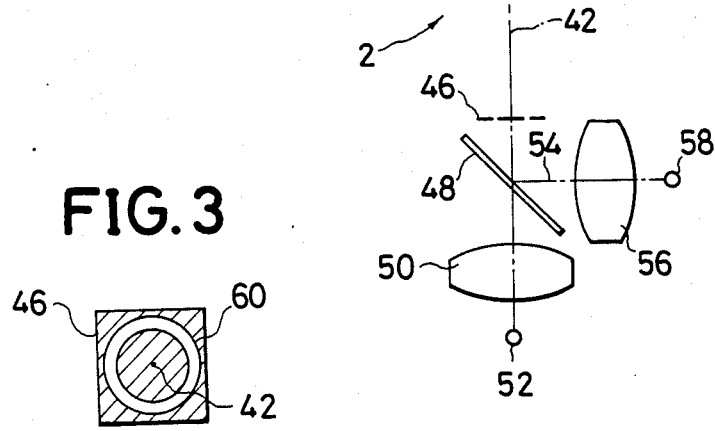
FIG.3
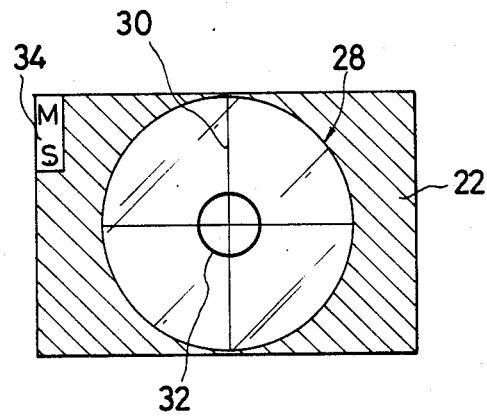
FIG.2
FIG.4
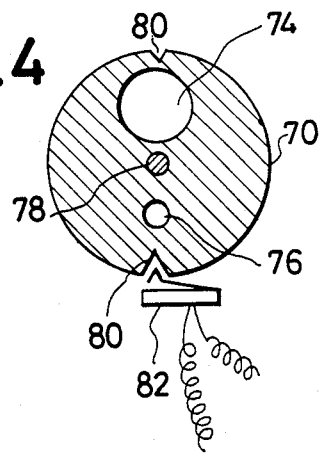

EYE FUNDUS CAMERA HAVING AUTOMATIC EXPOSURE CONTROL MEANS

This application is a continuation of application Ser. No. 015,556, filed on Feb. 12, 1987, which, in turn, is a continuation application of Ser. No. 598,842 filed Apr. 10, 1984, both now abandoned.

This invention relates to an eye fundus camera, and in particular to an eye fundus camera having automatic exposure control.

In an eye fundus camera, exposure must be optimized for photographing according to a kind of photographing and a film used therefor. In consideration of a difference in type of photographing such as a color or monochromatic photographing, an ordinary instant or fluorescent photographing, and also a difference in photosensitivity of the film an operator must usually adjust the intensity of photographing light source by means of an adjusting switch or the like before photographing. However, such adjustment may involve a trouble in most cases, and in addition an improper adjustment may cause an improper exposure. On the other hand, the pupil of the eye and a reflection factor of the eye fundus vary among patients, so that an optimum photographing condition of one patient's eye does not necessarily satisfy the photographing condition for another patient's eye.

In view of the above situation, there has already been proposed an eye fundus camera incorporating an automatic exposure control system which measures a reflected light from the eye fundus. However, in the exposure control system of a conventional eye fundus camera, a photometric range of an eye fundus image is constant at all times, but cannot be adjusted in accordance with a change in the photographing field.

It is therefore an object of the present invention to provide an eye fundus camera in which the aformentioned problems are solved.

Another object of the present invention is to provide an eye fundus camera having an automatic exposure control system in which light measurement can be carried out in a field which varies in accordance with a change in the photographing field.

According to the present invention, the above and other objects can be accomplished by an eye fundus camera comprising an illuminating optical system having photographing light source means for projecting luminous flux to a fundus of an patient's, photographing optical system having a photographing film plane and lens for forming an image of the fundus of the patient's eye, a light measuring system including reflecting means disposed in said photographing optical system for reflecting at least a part of light beams passing through said photographing optical system and optical detecting means for detecting the light beams reflected at said reflecting means, said light measuring means further including variable aperture means located in front of said optical detecting means and conjugate with said film plane in said photographing optical system, exposure control means responsive to a signal from said light measuring system for controlling film exposure to obtain an appropriate exposure in accordance with an intensity of light beams passing through the photographing optical system. According to the features of the present invention, the variable aperture means makes it possible to accomplish exposure measurement in a field corresponding to a photographing field. The aperture means may include an aperture plate having a plurality of apertures of different diameters, the aperture plate being mounted movably so that one of the apertures can be brought into an optical path to said optical detecting means. The exposure control means may include means for controlling the light source means to change intensity of light emitted therefrom.

The above and other objects and features of the present invention will become apparent from the following descriptions of preferred embodiments taking reference to the accompanying drawings, in which:

FIG. 1 is a diagrammatical illustration of an optical system of an eye fundus camera in accordance with a first embodiment of this invention;

FIG. 2 is a plan view of a focal plate;

FIG. 3 is a plan view of a ring chaped aperture;

FIG. 4 is a plan view of a variable aperture;

Figure 5:
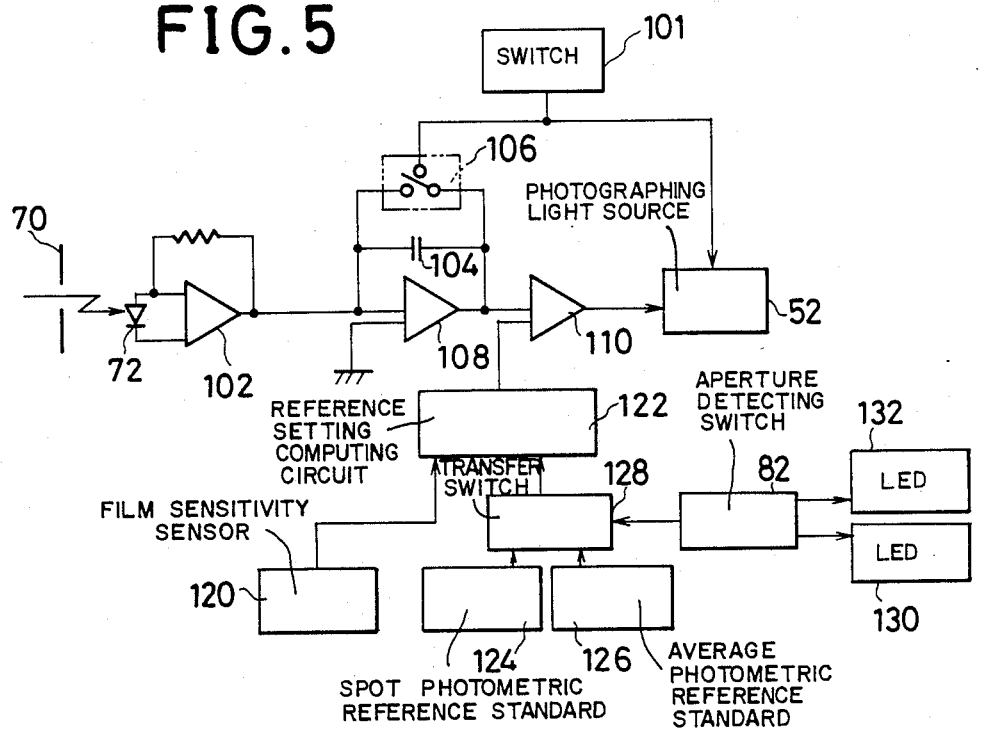
FIGS. 5 and 6 are block diagrams of a stroboscope control system.

Referring now to the drawings, particularly to FIG. 1, there is shown an optical system of an eye fundus camera 1 which comprises an observation photographing system 4 for observing and photographing an eye fundus $E_R$ of a patient's eye, an illuminating system 2 for illuminating the eye fundus $E_R$, and a light measuring or photometric system 6.

The observation photographing system 4 has an object lens 10, a focusing lens 12 movable along an optic axis 8 of the object lens 10 which passes through a patient's eye pupil $E_p$, for focusing, a circular photographing aperture 11, an image forming lens 14, a retractable mirror 16, and a film 18, which are disposed along the optic axis 8 in that order from a side of the patient's eye E. Then, a focal plate 22, a retangular prism 24 and an eye-piece lens 26 are disposed on a finder optic axis 20 which is a reflected optic axis of the retractable mirror 16 in that order from a side of the retractable mirror 16. The above members are disposed so that an image on the eye fundus $E_R$ be formed on a first image forming plane $E_E$ between the objective lens 10 and the focusing lens 12 and then formed on a film 18 by the focusing lens 12 and the image forming lens 14 and also on the focal plate 22 disposed conjugationally to the film F.

The retractable mirror 16 is positioned as indicated by a full line in FIG. 1 at the time of eye fundus observation, and a light from the eye fundus $E_R$ is reflected by the retractable mirror 16 formed on the focal plate 22. Then at the time of photographing, the retractable mirror 16 is shifted to a position indicated by a dotted line in FIG. 1, and the light from the eye fundus $E_R$ is formed on the film 18.

As shown in FIG. 2, the focal plate 22 has a central circular transparent part 28 representing a photographing field, cross lines 30 provided therein, a circular index 32 indicating a spot photometric range, and a photometric index 34. The photometrix index 34 has M indicating a photometry of an entire photographing field indicated on the central circular transparent part 28, namely a so-called average photometry and S indicating a photometry of the interior only of the circular index 32, namely a so-called spot photometry, and a light emitting diode (not illustrated in FIG. 2) is disposed on lower parts of the above-mentioned M and S each.

The illuminating system 2 has an apertured, slanted mirror 40 disposed between the objective lens 10 and the focusing lens 12 at a position substantially conjugate to the patient's eye pupil $E_p$, a relay lens 44, a ring aperture 46, a half mirror 48, a photographing condensor lens 50 and a photographing xenon lamp 52 which are disposed on an illuminating optic axis 42 which is a reflected optic axis of the mirror 40. On the reflected optic axis of the half mirror 48, there are an observing condenser lens 56 and an observing tungsten light source 58. As shown in FIG. 3, the ring aperture 46 has a ring-like slit 60 and is disposed at a position conjugate to the patient's eye pupil $E_p$ with reference to the objective lens 10 and the relay lens 44.

Illuminating beam from the illuminating system 2 passes through the objective lens 10 and the pupil $E_p$ to illuminate the eye fundus $E_R$. On the other hand, a photographing light beam from the eye fundus $E_R$ passes the patient's eye pupil $E_p$ and the central aperture of the mirror 40 and then reaches the film 18.

The photometric system 6 has a relay lens 66, a mirror 68, a variable aperture 70 and a photo detector 72 disposed at a position conjugate to the photographing aperture 11 for detecting intensity of incident light on a photometric optic axis 64 which is a reflected optic axis of a light splitting prism 62 disposed between the focusing lens 12 and the aperture 11. The prism 62 has a half mirror plane for reflecting a part of the observation photographing light beam. As shown in FIG. 4, the variable aperture 70 disposed at a position conjugate to the film 18 has a large circular aperture 74 corresponding to the central circular transparent part 28 of the focal plate 22 and a small circular aperture 76 corresponding to the circular index 32 thereof and limits the range of an incident light beam to the photo detector 72. Further, the variable aperture 70 is rotatable about a shaft 78 and puts the holes 74 and 76 selectively into the photometric optic axis 64.

When the small circular hole 76 is inserted, only a light beam from a field center of the eye fundus image comes into the photo detector 72 for a spot photometry. Then, when the large circular hole 74 is inserted, the light beam from an entire photographing field of the eye fundus image comes into the optical detector 72 for an average photometry. Thus, at least two kinds of photometry can be effected by the photo detector 72. In this embodiment, the above description has referred to the average photometry and the spot photometry, however, a photometry of a periphery only of the eye fundus image or a spot photometry of a portion other than the center of the eye fundus image can be selected arbitrarily, as occasion demands, by preparing further apertures. An aperture of a ring shape, for example, may allow a photometry of only the periphery other than the center.

Further, since the photo detector 72 is disposed at a position conjugate to the photographing aperture 11, an area of the light beam projected on the photo detector 72 is constant at all times and a light intensity in the light beam is averaged regardless of an aperture diameter of the variable aperture 70, and thus a stable photometric result is obtainable at all times.

A plurality of notches 80 are provided at suitable spots on a circumference of the variable aperture 70, and a selected one of the apertures 74 and 76 can be detected electrically by an aperture detecting switch 82 disposed near the variable aperture 70 to engage with the notches 80.

Next, descriptions will be made on an exposure control system for obtaining an optimum exposure through measuring photographing light, such control being carried out by controlling the photographing light source 52. Prior to photographing, the tungsten light source 58 is turned on, and the eye fundus $E_R$ is illuminated by a feeble light. An observing light reflected at the eye fundus $E_R$ passes the aperture of the mirror 40, reflects on the retractable mirror 16 positioned as indicated by a full line in FIG. 1, and then reaches the focal plate 22 to form an image of the eye fundus $E_R$. Observing the eye fundus image on the focal plate 22, the operator moves the focusing lens 12 to focus and also adjust the field of view.

When focusing and adjustment of the field of view are over, the shutter release button of the camera (not illustrated) is depressed. The retractable mirror 16 is then shifted first to a position indicated by a dotted line in FIG. 1, thus the photographing light reflected on the eye fundus $E_R$ reaching the film 18.

On the other hand, the xenon lamp 52 emits a light under the start signal from a switch 101 actuated according to the upward shifting of the retractable mirror 16. A part of the light beam from the eye fundus $E_R$ illuminated by the lamp 52 is reflected at the light splitting prism 62, passes the variable aperture 70 and then comes into the photo detector 72. An output of a current value corresponding to the quantity of incident light from the photo detector 72 is applied to a preamplifier circuit 102, converted into a voltage and then further given to an integrator 108 having a capacitor 104 and a discharging switch 106. The discharging switch 106 is turned on according to the start signal from the switch 101, thereby operating for start of integration on the integrator 108. An output of the integrator 108 is applied to a comparator 110.

The comparator 110 has a reference setting signal given from a reference setting computing circuit 122. ASA information from a film sensitivity setting part 120 and reference light quantity signal from a spot photometric standard 124 or an average photometric standard 126 are applied to the reference setting computing circuit 122. A transfer switch 128 is operated according to set aperture signal from the detecting switch 82 of the variable aperture 70. When the large circular aperture 74 is inserted, the reference light quantity signal from the average photometric standard 126 is applied to the reference setting computing circuit 122, and when the small circular aperture 76 is inserted, the reference light quantity signal from the spot photometric standard 124 is applied thereto.

The reference setting circuit 122 outputs the reference setting signal to the comparator 110 through arithmetic operation on these signals. The comparator 110 compares an integrated value from the integrator 108 with the reference setting signal from the reference setting circuit 122, and when both the signals become equal each other, it sends a stop signal to the lamp 52, thus turning the lamp off.

The set aperture signal from the detecting switch 82 is applied to light emitting diodes 130, 132 to illuminate a predetermined light emitting diode. The diodes 130, 132 are disposed in the photometric index 34 to illuminate selectively M or S in the index.

As described above, when the variable aperture 70 is operated to set a predetermined photometric range, an amount of photographing exposure is controlled most desirably in the photometric range, and the photometric range is indicated by a sign within the field of an observation system, which can be so confirmed by the photographer.

Figure 6:
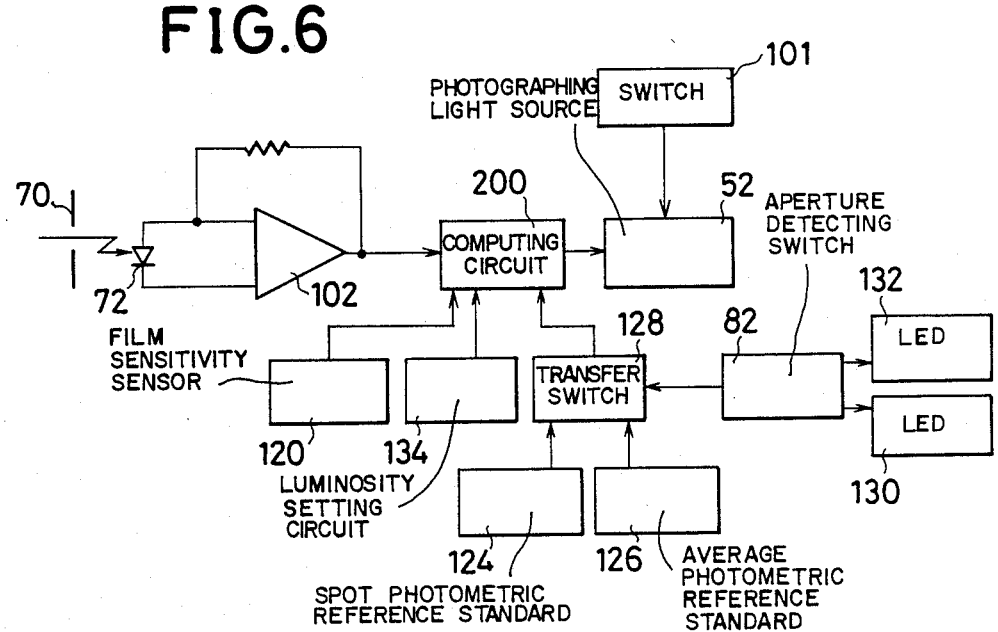

In the above embodiment, a description is given of the case where the amount of photographing exposure is controlled through measuring the quantity of photographing light directly, however, the amount of photographing exposure can also be controlled according to a result obtained through measuring a quantity of observing light. A xenon lamp control circuit in this case will be described with reference to a block diagram of FIG. 6. In this arrangement, the photo detector 72 is that for measuring a light from the eye fundus image illuminated by the observing tungsten light source 58, and parts common to FIG. 5 are identified by the same reference characters. A further description is omitted thereof accordingly.

A numeral 134 denotes a light source setting part for setting a luminosity of the observing light source, which operates for applying a signal corresponding to the set luminosity of light source to a computing circuit 200. The computing circuit 200 computes an optimum light emitting time according to the photometric range on a photometric signal from the pre-amplifier circuit 102, ASA information signal from the film sensitivity setting part 120, a reference light quantity signal given selectively by the transfer switch 128, applies a light emitting time setting signal to the lamp 52, and thus makes the lamp 52 ready for emitting light for a predetermined period of time for photographing.

Then in the above embodiment, it can be constituted that an insertion of the large circular aperture 74 by the variable aperture 70 may invite an extinction filter into a photometric optical path as inter-locking therewith, and the quantity of light coming into the photo detector 72 will be equalized at all times from inserting either the large circular aperture 74 or the small circular aperture 76. In this case, the reference light quantity signal described in FIGS. 5 and 6 can be set as constant irrespective of spot photometry and average photometry, thus simplifying the control circuit. In this case, further, a fluctuation of the quantity of light coming into the photo detector 72 is minimized, and a stable photometry is obtainable at high precision.

Figure 7:
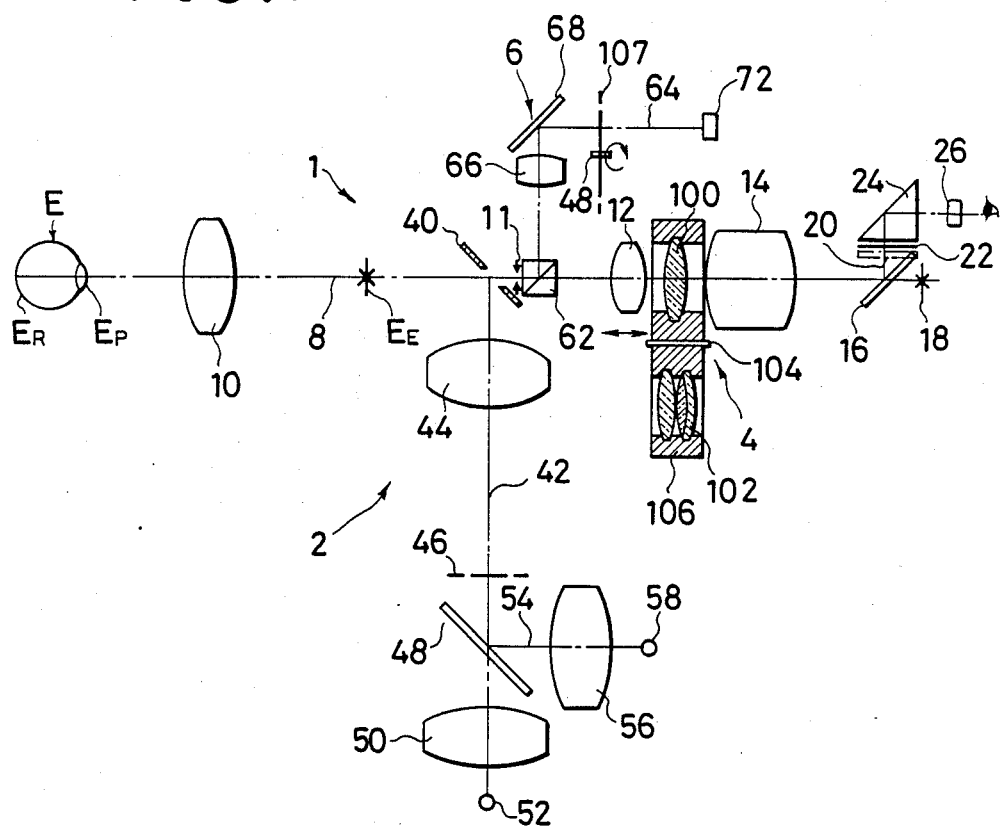
FIG. 7 is a diagrammatical illustration of an optical system of a second embodiment of this invention.
Figure 8:
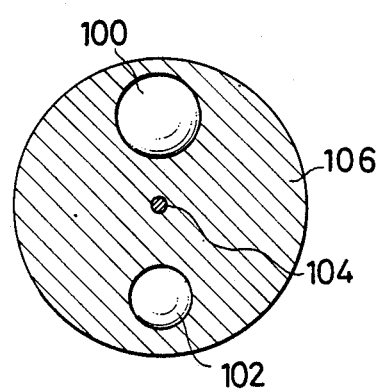
FIG. 8 is a plan view of a variable magnification lens board.

The second embodiment of this invention refers to an eye fundus camera of variable magnification as shown in FIG. 7, however, a further description will be omitted of such configuration as is same as the first embodiment, which is identified by the same reference character as the first embodiment. Variable magnification lenses 100, 102 are disposed between the focusing lens 12 and the image forming lens 14 of the observation photographing system 4. As shown in FIG. 8, the variable magnification lenses 100, 102 are fitted in a variable magnification lens board 106 rotatable round a shaft 104. The lenses 100, 102 can be inserted into the observation photographing optical axis 8 selectively.

Figure 9:
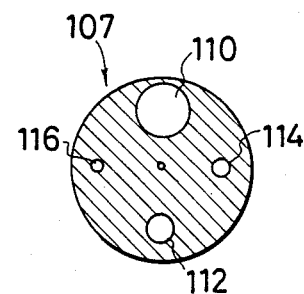
FIG. 9 is a plan view of a variable aperture.

A variable aperture 107 in the photometric system 6 comprises, as shown in FIG. 9, apertures 110, 112 corresponding to the lens 100 and apertures 114, 116 corresponding to the lens 102. When the variable magnification lens 100 or 102 is inserted into the observation photographing optical axis 8, the apertures 110, 112 or the apertures 114, 116 corresponding to the variable magnification lenses are made ready for insertion into the photometric optical axis 64.

The aperture 110 has a diameter large enough to correspond to a field of view of the eye fundus image indicated by the central circular transparent part 28 of the eye fundus image on the focal plate 22 when the variable magnification lens 100 is inserted onto the observation photographing optical axis 8, and is inserted in the photometric optical path for average photometry on the variable magnification lens 100. The aperture 114 has a diameter large enough to correspond to a field of view of the eye fundus image indicated by the circular index 32 on the focal plate 22 when the variable magnification lens 100 is inserted, and is inserted in the photometric optical path for spot photometry on the variable magnification lens 100. Similarly, the apertures 112, 116 have diameters for average photometry and spot photometry corresponding to the variable magnification lens 102. According to such configuration as mentioned, a change, if any, in the field of view for photographing by the variable magnification lenses may still ensure average photometry or spot photometry corresponding thereto.

Figure 10:
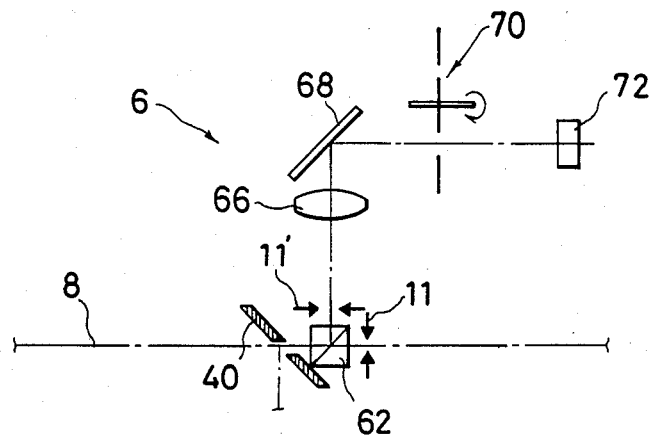
FIGS. 10 and 11 are diagrammatical illustration of optical systems of further embodiments of this invention.

FIG. 10 represents another embodiment of the photometric system 6 in this invention, however, a further description will be omitted, since the arrangement is substantially identical to that in FIG. 1. What is different from the embodiment of FIG. 1 is that since the light splitting prism 62 is disposed in front of the photographing aperture 11, an aperture 11' is provided on the photometric system 6 at a position conjugate to the photographing aperture 11, and the photo detector 72 is disposed conjugably to the aperture 11'.

Figure 11:
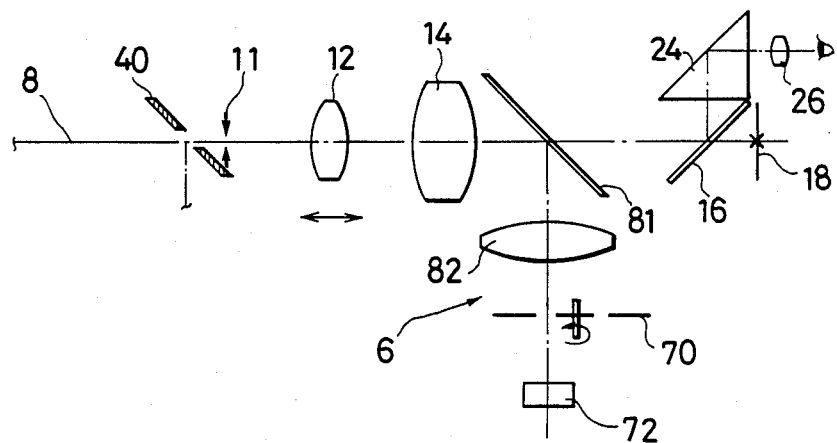

FIG. 11 represents a further embodiment of the photometric system 6 in this invention, however, a further description will be omitted since the arrangement is substantially identical to that shown in FIG. 1. In this embodiment, the photometric system 6 comprises a half mirror 81 disposed rear of the focusing lens 12 and the image forming lens 14. The light partly reflected at the half mirror 81 comes into the photo detector 72 through the relay lens 82 and the variable aperture 70 and measured by the photo detector 72. As in the case of the embodiment described in FIG. 1, the variable aperture 70 is disposed at a position conjugate to the film plane 18, and the photo detector 72 is disposed at a position conjutate to the photographing aperture 11.

The invention has thus been shown and described with reference to specific embodiments, however, it should be noted that the invention is in no way limited to the details of the illustrated arrangements but changes and modifications may be made within the scope of the appended claims.

I claim:

1. An eye fundus camera with automatic exposure control comprising an illuminating optical system having photographing light source means and observing light source means for projecting, respectively, photographing and observing luminous flux to a fundus of a patient's eye, said light being reflected by the eye along an optic axis, an observation-photographing optical system having a photographing film plane disposed on said axis, lens means for forming a photographic field image of the fundus of the patient's eye and finder means for observing the eye fundus including a plurality of observable indices corresponding to a plurality of measurable photometric ranges, a light measuring system including reflecting means disposed in said photographing optical system for reflecting at least a part of light beams passing through said photographing optical system and optical detecting means for detecting the light beams reflected at said reflecting means to produce a light intensity signal, said light measuring system further including selectively variable aperture means having a plurality of apertures of differing diameters corresponding to said plurality of measurable photometric ranges, said variable aperture means being located in front of said optical detecting means and conjugate with said film plane in said photographing optical system for providing an aperture of a selected diameter corresponding to the photometric range to be measured and means for indicating said selected aperture diameter, exposure control means including means responsive to said selected aperture diameter indicating means in said light measuring system for supplying a selected one of a plurality of reference signals corresponding to said plurality of measurable photometric ranges to control means responsive to said reference signal and said light intensity signal for controlling film exposure to obtain an appropriate exposure in accordance with an intensity of light beams passing through the photographing optical system.

2. An eye fundus camera in accordance with claim 1 in which said aperture means includes an aperture plate formed with said plurality of apertures adapted to be selectively positioned in front of the optical detecting means.

3. An eye fundus camera in accordance with claim 2 in which said aperture plate is a circular disc which is rotatable to put a selected one of the apertures in front of the optical detecting means.

4. An eye fundus camera with automatic exposure control comprising an illuminating optical system having photographing light source means and observing light source means for projecting, respectively, photographing and observing luminous flux to a fundus of a patient's eye, said light being reflected by the eye along an optic axis, an observation-photographing optical system having a photographing film plane disposed on said axis, lens means including a plurality of variable magnification lenses selectively placeable in said optic axis ford on said axis, lens means including a plurality of variable magnification lenses selectively placeable in said optic axis for forming a selected photographic field image of the fundus of the patient's eye corresponding to a selected one of said plurality of magnification lenses, and finder means for observing the eye fundus including a plurality of observable indices corresponding to a plurality of measurable photometric ranges, a light measuring system including reflecting means disposed in said photographing optical system for reflecting at least a part of light beams passing through said photographing optical system and optical detecting means for detecting the light beams reflected at said reflecting means to produce a light intensity signal, said light measuring system further including selectively variable aperture means having, for each of said plurality of magnification lenses, a plurality of apertures of differing diameters corresponding to said plurality of measurable photometric ranges, said variable aperture means being located in front of said optical detecting means and conjugate with said film plane in said photographing optical system for providing an aperture of a selected diameter corresponding to the photometric range to be measured and means for indicating said selected aperture diameter, exposure control means including means responsive to said selected aperture diameter indicating means in said light measuring system for supplying a selected one of a plurality of reference signals corresponding to said plurality of measurable photometric ranges to control means responsive to said reference signal and said light intensity signal for controlling film exposure to obtain an appropriate exposure in accordance with an intensity of light beams passing through the photographing optical system.

5. The eye fundus camera according to claims 1 or 4 wherein said finder means further comprises means for indicating the photometric range being measured.

* * * * *

UNITED STATES PATENT AND TRADEMARK OFFICE
CERTIFICATE OF CORRECTION

PATENT NO. : 4,834,526
DATED : May 30, 1989
INVENTOR(S) : Kazuo Nunokawa

It is certified that error appears in the above-identified patent and that said Letters Patent is hereby corrected as shown below:

Column 1, line 49, after "patient's" insert --eye--;

Column 4, line 47, after "to" insert --a--;

Column 8, lines 1-2, delete "lens means including a plurality of variable magnification lenses selectively placeable in said optic axis ford on said axis,".

Signed and Sealed this

Twenty-eighth Day of August, 1990

Attest:

HARRY F. MANBECK, JR.

*Attesting Officer*  *Commissioner of Patents and Trademarks*